United States Patent [19]
Garsky

[11] 3,971,737
[45] July 27, 1976

[54] [2-METHYL-Ala⁶]LRH

[75] Inventor: Victor M. Garsky, Havertown, Pa.

[73] Assignee: American Home Products Corporation, New York, N.Y.

[22] Filed: Mar. 24, 1975

[21] Appl. No.: 561,525

[52] U.S. Cl. .................. 260/112.5 LH; 424/177
[51] Int. Cl.² ................. C07C 103/52; A61K 37/26
[58] Field of Search .................... 260/112.5 LH

[56] References Cited
UNITED STATES PATENTS

| | | | |
|---|---|---|---|
| 3,855,199 | 12/1974 | Foell et al. | 260/112.5 LH |
| 3,886,135 | 5/1975 | McKinley et al. | 260/112.5 LH |
| 3,886,137 | 5/1975 | Yardley | 260/112.5 LH |

OTHER PUBLICATIONS

Monahan et al.: Biochem. 12, 4616–4620, (1973).

*Primary Examiner*—Lewis Gotts
*Assistant Examiner*—Reginald J. Suyat
*Attorney, Agent, or Firm*—Richard K. Jackson

[57] ABSTRACT

[2-Methyl-Ala⁶]LRH is described, as well as its preparation by solid phase methodology and intermediates in its production. The decapeptide is a luteinizing hormone releasing agent and is useful as an ovulation inducing agent and as a claudogenic/interceptive agent.

4 Claims, No Drawings

[2-METHYL-ALA⁶]LRH

RELATED APPLICATIONS

Copending application Ser. No. 526,344, filed Nov. 22, 1974 discloses and claims [D-Phe², 2-methyl-Ala⁶]LRH as an anti-ovulatory agent. Copending, concurrently filed application Ser. No. 561,524 of Alan Corbin, now abandoned, entitled "Use of LRH and LRH Agonists" discloses and claims the method of effecting a claudogenic/interceptive response employing [2-methyl-Ala⁶]LRH in a placental mammal.

BACKGROUND OF THE INVENTION

Luteinizing hormone releasing hormone (LRH) is a decapeptide presenting the following amino acid sequence:

p-Glu-His-Trp-Ser-Tyr-Gly-Leu-Arg-Pro-Gly-NH$_2$.

LRH is secreted by the hypothalamus and stimulates secretion of the pituitary hormone(s) known to regulate ovulation. Several modifications of LRH have been produced. Fujino et al., Biochem. Biophys. Res. Comm. 49, pp. 698–705 (1972). One modification of LRH recently produced is [D-Ala⁶]LRH. Monahan et al., Biochemistry, Vol. 12, No. 23, 4616 (1973).

DESCRIPTION OF THE INVENTION

In accordance with this invention, there is provided the decapeptide [2-methyl-Ala⁶]LRH and non-toxic acid addition salts thereof, intermediates for its production and a process for its production via the solid phase method. The compound [2-methyl-Ala⁶]LRH presents the amino acid sequence:

L-p-Glu-L-His-L-Trp-L-Ser-L-Tyr-2-Me.Ala-L-Leu-L-Arg-L-Pro-Gly-NH$_2$, in which 2-Me.Ala represents the 2-methylalanyl $$-NH-\underset{\underset{CH_3}{|}}{\overset{\overset{CH_3}{|}}{C}}-CO-.$$

The intermediate peptides of this invention, which are useful in the production of [2-Me-Ala⁶]LRH are of the formula:

2—Me—Ala—Leu—Arg (N$^g$—R$^1$)—Pro-Gly—R wherein:

N$^g$ means the side chain nitrogen atoms of arginine;

N$^{im}$ means the nitrogen atoms of the imidazole ring of histidine:

R is selected from the class consisting of NH$_2$, OH, O-(lower)alkyl, in which (lower)alkyl is C$_1$ through C$_6$ (e.g., methyl, ethyl, pentyl, hexyl, etc.) and O-benzyl or a solid polystyrene resin support of the formula

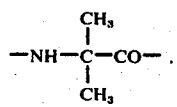—NHCH—(polystyrene resin support)

or —O—CH$_2$ (polystyrene resin support);

R$^1$ is a protecting group for the N$^\delta$, N$^\omega$ and N$^{\omega'}$ nitrogen atoms of arginine, selected from the class consisting of nitro, tosyl, benzyloxycarbonyl, adamantyloxycarbonyl and tert-butyloxycarbonyl; or R$^1$ is hydrogen which means there are no protecting groups on the side chain nitrogen atoms of arginine. Where the protecting group is nitro or tosyl, the protection is on either one of the N$^\omega$, N$^{\omega'}$ nitrogens and in the case of benzyloxycarbonyl, or adamantyloxycarbonyl, the protection is on the N$^\delta$ nitrogen and either one of the N$^\omega$, N$^{\omega'}$ nitrogen atoms. The preferred protecting group defined by R$^1$ is tosyl;

R$^2$ is a protecting group for the phenolic hydroxyl group of tryosine selected from the class consisting of tetrahydropyranyl, tert-butyl, trityl, benzyl, 2-6-dichlorobenzyl, benzyloxycarbonyl and 4-bromobenzyloxycarbonyl. The preferred protecting group is benzyl; or R$^2$ is hydrogen which means there is no protecting group on the phenolic hydroxy function;

R$^3$ is a protecting group for the alcoholic hydroxyl group of serine and is selected from the class consisting of acetyl, benzoyl, tetrahydropyranyl, tert-butyl, trityl, benzyl, 2,6-dichlorobenzyl, benzyloxycarbonyl or R$^3$ is hydrogen which means there is no protecting group on the alcoholic oxygen atom. Preferably R$^3$ is benzyl; and R$^4$ is a protecting group for the imidazole nitrogen atom of histidine selected from the group consisting of tosyl, benzyl, trityl, 2,2,2-trifluoro-1-benzyloxycarbonylaminoethyl and 2,2,2-trifluoro-1-tert-butyloxycarbonylaminoethyl or 2,4-dinitrothiophenyl.

The polystyrene resin support representing R is polystyrene crosslinked with about 1 to 2 percent divinyl benzene and subsequently treated to introduce the

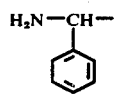

H$_2$N—CH— or HO—CH$_2$— functional groups, with which glycine is initially reacted to serve as the supported amino acid starting material from which the desired polypeptide is developed. In practice, α-amino protected glycine is reacted with a benzhydrylamine resin, a chloromethylated resin or a hydroxymethyl resin, the former being preferred. The preparation of benzhydrylamine resin is described by P. Rivaille et al., Helv. 54, 2772 (1971) and the preparation of the hydroxymethyl resin is described by Bodanszky et al., Chem. Ind. (London) 38, 1597–98 (1966). A chloromethylated resin is commercially available from Bio Rad Laboratories Richmond, California and the preparation of such a resin is described by Stewart et al., "Solid Phase Peptide Synthesis" (Freeman & Co., San Francisco 1969), Chapter 1, pp. 1–6. In using the benzhydrylamine resin an amide anchoring bond is formed with the α-amino protected glycine as follows:

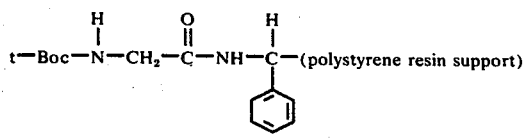

t—Boc—N(H)—CH$_2$—C(=O)—NH—C(H)—(polystyrene resin support)

This permits the terminal amide function to be obtained directly after the amino acid sequence in the synthesis is complete by cleaving off the resin support to form the glycyl amide. When the other resins are used, the anchoring bond is an ester group of glycine and the oxymethyl resin, which after cleavage of the peptide from the resin support is converted to the terminal amide. The preferred procedure is to ammonolyse the protected peptide from the resin and then remove the protecting groups by hydrogenolysis or by hydrogen fluoride cleavage. An alternate procedure would be to cleave by transesterification with methanol/(Et)$_3$N and then convert the resulting polypeptide ester into an amide and subsequently deprotect as described above. See J. M. Stewart "Solid Phase Peptide Synthesis," pp 42–46 (Freeman & Co. San Francisco 1969).

Therefore, the selection of a particular side chain protecting group to be used in the synthesis of the peptide of this invention, is made in accordance with the following rules: (a) the protecting group must be stable to the reagent and under the reaction conditions selected for removing the α-amino protecting group at each step of the synthesis, (b) the protecting group must retain its protecting properties, (i.e., not be split off under coupling conditions), and (c) the side chain protecting group must be removable upon the completion of the synthesis containing the desired amino acid sequence under reaction conditions that will not alter the peptide chain.

The α-amino protected glycine is coupled to the benzhydrylamine resin with the aid of a carboxyl group activating compound such as diisopropylcarbodiimide. Following the coupling of the α-amino protected glycine to the resin support, the α-amino protecting group is removed such as by using trifluoroacetic acid in dichloromethane, trifluoroacetic acid alone or HCl in dioxane. The deprotection is carried out at ambient temperature. Other standard cleaving reagents and conditions for removal of specific α-amino protecting groups, may be used as described in Schroder & Lubke, "The Peptides," 1 72–75 (Academic Press 1965). After removal of the α-amino protecting group the remaining α-amino protected amino acids are coupled step-wise in the desired order to obtain [2-methyl-Ala$^6$]LRH. However, as an alternate to adding each amino acid separately to the reaction, some of them may be coupled prior to addition to the solid phase reactor. Each protected amino acid or amino acid sequence, is introduced into the solid phase reactor in about a six-fold excess and the coupling is carried out in a medium of dimethylformamide: dichloromethane (1:1) or in dimethylformamide or dichloromethane alone. In cases where incomplete coupling occurs the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem., 34, 595 (1970).

The α-amino protecting groups which may be used in this process are those known to be useful in the art in the step-wise synthesis of polypeptides. Among the classes of α-amino protecting groups are (1) acyl type protecting groups illustrated by the following: formyl, trifluoroacetyl, phthalyl, toluenesulfonyl (tosyl), benzenesulfonyl, nitrophenylsulfenyl, tritylsulfenyl, O-nitrophenoxyacetyl, chloroacetyl, acetyl, γ-chlorobutyryl, etc.; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl (t-Boc), diisopropylmethoxycarbonyl, isopropyloxycarbonyl, ethoxycarbonyl, allyloxycarbonyl; (4) cycloalkyl urethane type protecting groups illustrated by cyclopentyloxycarbonyl, adamantyloxycarbonyl, cyclohexylocycarbonyl; (5) thio urethan type protecting groups such as phenyl thiocarbonyl; (6) alkyl type protecting groups as illustrated by triphenylmethyl (trityl), benzyl; (7) trialkylsilane groups such as trimethylsilane. The preferred α-amino protecting group in this synthesis is tert-butyloxycarbonyl.

After the desired amino acid sequence has been synthesized, the peptide is removed from the resin support by treatment with a reagent such as hydrogen fluoride which not only cleaves the peptide from the resin but also cleaves all remaining side chain protecting groups to obtain [2-methyl-Ala$^6$]LRH in the case where the benzhydrylamine resin was used. Where a chloromethylated resin is used the peptide may be separated from the resin by methanolysis after which the recovered product is chromatographed on silica gel and the collected fraction subject to ammonolysis to convert the methyl ester to the amide. Any side chain protecting group may then be cleaved as previously described or by other procedures such as catalytic reduction (e.g., Pd on Carbon) using conditions which will keep the Trp moiety intact. When using hydrogen fluoride for cleaving, anisole is included in the reaction vessel to prevent the oxidation of any labile amino acid (e.g., tryptophan).

The solid phase synthesis procedure discussed supra is well known in the art and has been essentially described by M. Monahan et al., C. R. Acad. Sci. Paris, 273, 508 (1971).

The nomenclature used for peptides is described by Schroder & Lubke, supra, pp vii–xxix and in Biochemistry 11, 1726–1732 (1972).

[2-Methyl-Ala$^6$]LRH is an active releaser of luteinizing hormone (LH). This fact was established, in vivo, by measuring the increase of LH (before and after administration of [2-methyl-Ala$^6$]LRH) in the blood serum of ovariectomized rats pretreated with estradiol and progesterone according to the procedure of Schally et al., J. Biol. Chem. 246, 7230 (1971). The LH concentration in the blood serum was determined by radioimmunoassy according to the procedure of Berson et al., Metabolism 13, 1135 (1964). The results of this test are as follows:

| Dose nanograms (ng) | Animal No. | ng LH/ml Pre | Serum Post | % Difference |
|---|---|---|---|---|
| 10 | 1 | 404.92 | 932.87 | 103.38 |
| 10 | 2 | 541.37 | 1062.03 | 96.17 |
| 10 | 3 | 441.25 | 1568.03 | 255.43 |
| 10 | 4 | 459.07 | 1082.72 | 135.85 |
| 10 | 5 | 759.11 | 1681.84 | 111.52 |
| No. of observations | | 5 | 5 | 5 |
| Mean | | 523.34 | 1265.56 | 145.87 |
| Standard error | | 70.34 | 150.08 | 28.28 |
| T-value | | | | 5.1586 |
| P-value | | | | 0.0080 |

Thus, [2-methyl-Ala⁶]LRH is an active LRH agonist and is useful, as is LRH itself, for the purpose of inducing ovulation in the placental mammal. By analogy with other known LRH agonists, [2-methyl-Ala⁶]LRH may be administered either orally or parenterally, the oral dose being normally greater than that used intravenously, subcutaneously or intramuscularly. The typical dosage form for LRH and LRH agonists is in physiological saline solution. Oral administration is conventional in either liquid or solid form, neat or in the presence of conventional pharmaceutical adjuvants.

[2-methyl-Ala⁶]LRH has been found by Alan Corbin (copending application Ser. No. 561,524) to be an active claudogenic/interceptive agent, preventing 100 percent of pregnancies at a dose of 500 micrograms per day when administered to Sprague-Dawley rats in accordance with the following procedure: Female, Sprague-Dawley rats, 200–250 g., are caged daily (P.M.) with adult, sexually experienced Sprague Dawley males. Vaginal smears are taken each A.M. after cohabitation. The presence of vaginal sperm is used as the index of mating and initiation of pregnancy. Day 1 of pregnancy is taken as the day sperm is found in the vaginal smear. Mated females are then grouped separately. Treatment is begun at any time over the first 12 days of pregnancy and a divided dose (9 A.M. and 3 P.M.) or a single treatment. Claudogenic activity is defined for compounds administered over the first 7 days inclusive of pregnancy (Pre-implantation). Interceptive activity is defined for compounds administered days 7–12 inclusive of pregnancy (Post-implantation). Rats are sacrificed on D 14 (claudogen), D 18 (interceptive) or allowed to come to term prior to sacrifice (claudogen or interceptive). Rats containing at least one "Normal" fetus are considered pregnant.

Based upon the known similarities between the rat and the human fertility gestation system, the decapeptide of this invention — [2-methyl-Ala⁶]LRH is established as an effective claudogenic/interceptive agent for use in the menstruating mammal.

The following Examples illustrate the process of this invention in the preparation of the intermediate and final product [2-methyl-Ala⁶]LRH:

EXAMPLE I

L-(5-oxoprolyl)-N$^{im}$-tosyl-L-histidyl-L-tryptophyl-O-benzyl-L-seryl-0-2,6-dichlorobenzyl-tyrosyl-2-methylalanyl-L-leucyl-N$_g$-tosyl-L-arginyl-L-prolylglycyl benzhydrylamine resin Benzhydrylamine hydrochloride resin (10.0 g., 5.3 m moles) is placed in a Beckman 990 peptide synthesizer reaction vessel and treated in the following manner:

1. methylene chloride (three times)
2. 5 minute prewash with 1:1 trifluoroacetic acid-methylene chloride (v/v) containing 0.5% dithioerythritol
3. 30 minute deprotection with the above described trifluoroacetic acid
4. methylene chloride (six times)
5. 15% triethylamine in dimethylformamide (three times)
6. methylene chloride (six times)

A contact time of 1.5 minutes is allowed for each wash unless otherwise indicated.

The resin is gently stirred with tertiary butyloxycarbonyl glycine (5.6 g., 31.8 m moles in methylene chloride) and 35.0 ml. of 1 M diisopropylcarbodiimide (DIC) in methylene chloride (DIC added in two portions over 30 minutes). After stirring for 18 hours the peptide-resin is washed successively with methylene chloride (three times), dimethylformamide (three times) and methylene chloride (three times). Any unreacted sites are acylated with acetylimidazole (60 ml., 2.5% in methylene chloride) for 30 minutes and the resin washed with methylene chloride (six times).

The deprotection of the attached amino acid is carried out as described in steps (1) through (6) above.

The following amino acid residues are then introduced consecutively: tertiary butyloxycarbonyl-L-proline (6.8 g., 31.8 m moles in methylene chloride, 35 m moles DIC), tertiary butyloxycarbonyl-L-N$^a$-tosyl-L-arginine (11.2 g., 31.8 m moles in dimethylformamide, 35 m moles DIC), tertiary butyloxycarbonyl-L-leucine monohydrate (7.9 g., 31.8 m moles in methylene chloride, 35 m moles DIC), tertiary butyloxycarbonyl-α-aminoisobutyric acid 6.3 g., 31.8 m moles in methylene chloride, 35 m moles DIC), tertiary butyloxycarbonyl-0-2,6-dichlorobenzyl-L-tyrosine (15.0 g., 31.8 m moles in dimethylformamide, 35 m moles DIC), tertiary butyloxycarbonyl-O-benzyl-L-serine (9.4 g., 31.8 m moles in methylene chloride, 35 m moles DIC), tertiary butyloxycarbonyl-L-tryptophane (9.7 g., 31.8 m moles in dimethylformamide, 35 m moles DIC). Reaction time for each coupling is 3 hours. Following each coupling the peptide-resin is washed and acylated as described above. Removal of the α-amino protecting group at each step is performed as described for the deprotection of the tertiary butyloxycarbonylglycine-resin (steps 1–6). The washed octapeptide-resin is dried, weighed (16.6 g.) and the synthesis continued with 19% (3.2 g., 1.0 m moles) of the peptide-resin. The next amino acid added is tertiary butyloxycarbonyl-N$^{im}$-tosyl-L-histidine (2.5 g., 6 m moles in 50% methylene chloride-dimethylformamide, 7.2 m moles DIC) followed by L-2-pyrrolidone-5-carboxylic acid (1.0 g., 8 m moles in dimethylformamide, 9.6 m moles DIC). The washed decapeptide resin is dried in vacuo to yield 2.6 g.

EXAMPLE II

L-(5-oxoprolyl)-L-histidyl-L-tryptophyl-L-seryl-L-tyrosyl-2-methylalanyl-L-leucyl-L-arginyl-L-prolyl-glycinamide The compound of Example I (2.6 g.) is treted in vacuo with anhydrous liquid hydrogen fluoride (70 ml.) and anisole (10 ml.) at 0° for 45 minutes. The hydrogen fluoride and anisole are removed under reduced pressure and the residue suspended in 50% acetic acid. After filtration the filtrate is extracted with hexane and the aqueous phase lyophilized to leave the above titled product (0.95 g).

EXAMPLE III

Purification and characterization of L-(5-oxoprolyl)-L-histidyl-L-tryptophyl-L-seryl-L-tyrosyl-2-methylalanyl-L-leucyl-L-arginyl-L-prolyly-glycinamide The crude product from Example II is purified as follows: 0.95 g. of this product is dissolved in a minimum amount of 2 N acetic acid and applied to a column (2.5 × 100 cm.) of Sephadex G-15 medium in 2 N acetic acid. The column is eluted with 2 N acetic acid and 2.5 ml. fractions collected. Tubes 120–130 are shown to be homogenous by thin layer chromatography systems 4:1:5 (N-butanol-acetic acid-water) $R_f$ 0.30, and 7:7:6 (isoamyl alcohol:pyridine:water) $R_f$ 0.60, on silica gel G. Thin layer chromatograms are visualized with iodine and chlorine peptide reagent.

After hydrolysis of the peptide (6 N HCl, 4% thioglycolic acid) for 20 hours at 110° in a closed system under nitrogen, the following values for the product are obtained; Glu 0.96, His 0.95, Trp 0.85, Ser 0.66, Tyr 0.97, 2-Me.Ala 0.95, Leu 0.94, Arg 0.97, Pro 1.03, Gly 1.00.

What is claimed is:

1. A compound selected from the group consisting of L-p-Glu-L-His-L-Trp-L-Ser-L-Tyr-2-methyl-Ala-L-Leu-L-Arg-L-Pro-Gly-NH$_2$ and L-p-Glu-L-His(N$^{im}$-R$^4$)-L-Trp-L-Ser(R$^3$)-L-Tyr(R$^2$)-2-methyl-Ala-L-Leu-L-Arg(N$^g$-R$^1$)-L-Pro-Gly-R and non-toxic salts thereof; wherein;

R is a member selected from the group consisting of —NH$_2$, —OH, —O(lower)alkyl of 1 to 6 carbon atoms, —O—benzyl,

and —OHC$_2$—(polystyrene support resin);

R$^1$ is a member selected from the group consisting of —H and a protecting group for the N$^\delta$, N$^\omega$ and N$^{\omega'}$ nitrogen atoms of arginine selected from nitro, tosyl, benzyloxycarbonyl, adamantyloxycarbonyl and tert-butyloxycarbonyl;

R$^2$ is selected from the class consisting of hydrogen and a protecting group for the phenolic hydroxyl group of tyrosine selected from tert-butyl, tetrahydropyranyl, trityl, benzyl, 2,6-dichlorobenzyl, benzyloxycarbonyl and 4-bromobenzyloxycarbonyl;

R$^3$ is selected from the class consisting of hydrogen and a protecting group for the alcoholic hydroxyl group of serine and is selected from acetyl, benzoyl, tetrahydropyranyl, tert-butyl, trityl, 2,6-dichlorobenzyl, benzyl and benzyloxycarbonyl; and R$^4$ is selected from the group consisting of hydrogen and a protecting group for the imidazole nitrogen atom of histidine selected from tosyl, benzyl, trityl, 2,4-dinitrothiophenyl, 2,2,2-trifluoro-L-benzyloxycarbonylaminoethyl and 2,2,2-trifluoro-L-butyloxycarbonylaminoethyl.

2. A compound according to claim 1 wherein R is NH$_2$.

3. A compound according to claim 1 wherein R is NH$_2$, R$^1$ is tosyl, R$^2$ is 2,6-dichlorobenzyl, R$^3$ is benzyl and R$^4$ is tosyl.

4. A compound according to claim 1 which is selected from L-pyroglutamyl-L-histidyl-L-tryptophyl-L-seryl-L-tyrosyl-2-methylalanyl-L-leucyl-L-arginyl-L-prolyl-glycinamide and its non-toxic acid addition salts.

* * * * *